United States Patent [19]
Martz

[11] Patent Number: 6,071,834
[45] Date of Patent: *Jun. 6, 2000

[54] DIMENSIONALLY STABILIZED BREATHABLE MEMBRANE

[76] Inventor: Joel D. Martz, 5 Seally Dr., Lawrence, N.Y. 11559

[ * ] Notice: This patent is subject to a terminal disclaimer.

[21] Appl. No.: 08/906,790

[22] Filed: Aug. 9, 1997

Related U.S. Application Data

[63] Continuation-in-part of application No. 08/343,195, Nov. 22, 1994, Pat. No. 5,656,167.

[51] Int. Cl.⁷ .................................................. B01D 69/12
[52] U.S. Cl. .................................. 442/51; 442/57; 442/58; 442/394; 428/107; 210/490; 210/500.27; 156/178
[58] Field of Search .................................. 442/51, 57, 58, 442/394; 428/107; 210/490, 500.35, 500.36, 500.27, 500.28; 156/177, 178, 291

[56] References Cited

U.S. PATENT DOCUMENTS

| | | |
|---|---|---|
| 3,444,025 | 5/1969 | Hillas . |
| 3,751,329 | 8/1973 | Fonzi et al. . |
| 3,949,111 | 4/1976 | Pelletier . |
| 4,433,026 | 2/1984 | Molde . |
| 4,507,356 | 3/1985 | Watabe . |
| 4,808,675 | 2/1989 | Twilley et al. . |
| 4,898,761 | 2/1990 | Dunaway et al. . |
| 5,342,469 | 8/1994 | Bodford et al. . |

*Primary Examiner*—Christopher Raimund
*Attorney, Agent, or Firm*—David M. Warren

[57] ABSTRACT

A breathable membrane and a method of constructing a fabric having the membrane, wherein the membrane is resistive to transport of liquid water, has a layer of breathable material and is stabilized dimensionally against distension by a force field, such as forces which may be applied to the membrane or resulting from a hydrostatic pressure, by a reinforcing matrix of nonwoven filaments extending in plural directions along the layer of breathable material to inhibit the distension. In the matrix, the filaments are arranged in a first plurality of the filaments which intersect a second plurality of the filaments to form cells. A minimum diameter of an individual one of the cells is greater by at least approximately an order of magnitude than a diameter of one of the filaments to provide open areas of the layer of breathable material which are free from obstruction by the filaments. The membrane is suitable for construction of a surgical gown or drape preventing transmission of pathogens, a covering for a wall of a house, as well as a covering of a container for industrial processes. The matrix filaments may be constructed in elastic form, but wherein the elasticity of each filament is limited for a maximum amount of extension so as to avoid any rupture of the breathable film. The extension limits may be the same or may differ among the various filaments.

18 Claims, 5 Drawing Sheets

DIMENSIONALLY STABILIZED BREATHABLE MEMBRANE

RELATED APPLICATION

This application is a continuation-in-part of application Ser. No. 08/343,195 filed Nov. 22, 1994, now U.S. Pat. No. 5,656,167.

BACKGROUND OF THE INVENTION

This invention relates to a moisture vapor permeable membrane and, more particularly, to a reinforcing of the membrane for dimensional stability which renders the membrane suitable for construction of a surgical gown or drape, a covering for a wall of a house, as well as a covering of a container for industrial processes.

Moisture vapor permeable membranes in the form of films may be made from synthetic polymers and formed by casting, extrusion or other known film-making processes. Film thickness is in a range of typically 0.5–10 mils and preferably in a range from 0.6–3 mils. The films are continuous and are formed generally of hydrophilic polymeric materials through which water vapor is capable of diffusing. Such films may be of a plastic material such as copolyether polyester, or polyurethane or acrylate copolymers as disclosed in McCracken et al, U.S. Pat. No. 4,413,621. One form of such film is referred to as a monolithic film, and has no holes produced therein by a physical processing of the film but, rather, has passages with cross-sectional sizes on a molecular scale formed by a polymerization process and serving as conduits by which water molecules can propagate through the film. A second form of the film is known as a microporous film, and has microscopic holes produced therein by a physical stretching of the film provided during construction of the film. In certain applications wherein increased flow of fluid through the film is required, an array of holes punched by fine needles may be provided within the film; however, the cross-sectional dimensions of such holes are larger by many orders of magnitude than the passages of microporous and monolithic films. Generally, the microporous and monolithic films have moisture vapor transfer rates between 15 and 80 grams per 100 square inches per 24 hour interval at a temperature of 100° Fahrenheit and 90% Relative Humidity.

By way of example in the use of such films, benefits of the film have been demonstrated by use of the film as a surgical dressing as disclosed in Martz, U.S. Pat. No. 4,846,164. The surgical dressing may be constructed as a laminate including a layer of the film with a gauze pad for absorption of exudate from a patient, and wherein the laminate may include also some form of backing layer to facilitate exposure of an adhesive surface for emplacement of the dressing on a wound. The film is impermeable to liquid water and to bacteria so as to form a very effective shield which protects a patient from sources of infection external to the skin. The film retains body fluids within the body at the site of the wound. The vapor permeability of the film provides a sufficient rate of water vapor transport through the film to allow the skin to breathe normally, and is useful, therefore, not only in the construction of dressings, but also in the construction of garments wherein the characteristic of vapor permeability gives a cool feel rather than a sensation of excess heat. The film has sufficient elasticity to conform to the shape of various parts of the body, even a flexible body part such as a knee or elbow. Both the film and the adhesive layer may be constructed to be transparent or opaque as may be desired for particular applications of the film. Materials used in the construction of the film are non-allergenic.

The foregoing benefits in the use of the membrane are not restricted to surgical dressings, but can be employed to advantage in the construction of a much larger covering, such as a surgical drape or gown which may be large enough to cover part or all of a person. For example, a physician wearing a surgical gown made of a membrane, such as the foregoing film, would experience comfort provided by the breathability of the film, and would be protected from bacterial and even viral infection because of the capacity of the film to shield a person from such sources of infection. The flexibility of the film would allow the physician to move about freely, as is required in the performance of surgical procedures, by way of example. Thus, a film or membrane having the foregoing properties of being breathable and impervious to liquid water would offer protection from liquids, particularly body fluids such as blood which may carry pathogens, microbes, and other extraneous contaminants which may be injurious to the health of a health care worker.

In spite of the many advantages of the thin film type of membrane, there are problems associated with its use. The film is too thin to be handled without some form of backing sheet because the extreme flexibility and limpness allow the film to curl over upon itself. Such difficulty is compounded in the event that an adhesive layer be present on a surface of the film, as might be done to provide for lamination of the film in a manufacturing process. Furthermore, the film is fragile and may catch readily upon a sharp or rough object resulting in a tearing of the film and a loss of the integrity of the film as a barrier to pathogens. Even if some sort of permanent backing layer be applied to the membrane for increased stiffness and resistance to abrasion, then a further problem is introduced, namely, that such backing layer may materially alter the vapor transport rate of the membrane and, depending on the nature of the backing layer, may not allow for any vapor transport. Thus, there are significant disadvantages in the use of such a thin-film membrane for use by health care workers, as well as disadvantages in the handling of such membrane for fabricating products incorporating the membrane.

A further aspect in the use of such membrane or film may be appreciated from a standardized textile test similar to the Mullens test, for example, a standardized test such as ASTM, ES 21 and 22 for measurement of potential penetration by blood which may contain pathogenic microorganisms through a membrane under conditions wherein a hydraulic pressure is applied across a surface of the membrane. Under a pressure of two pounds per square inch, excessive bowing of the film is noted in a test cell diameter of only three inches. The bowing is associated with cold flow, elongation and creep of the plastic breathable material, and produces such a distension of the film that there is danger of rupture as well as, possibly, a change in the physical parameters of the film. For example, any tear produced by the distension would permit a flow of liquid through the film, thus negating resistance of the film to passage of liquid water and blood borne pathogens. In order to prevent such failure to the film under test, the test procedure allows for the use of a metal or plastic grid to support the film against the hydrostatic pressure, and thereby prevent the bowing.

The foregoing bowing and impairment of the film under hydrostatic pressure can appear in other cases of unsupported film as may be demonstrated for various situations in the wearing of garments. For example, a surgeon having his arm covered by such a film may accidentally press his arm against a blood covered surface of a table or other fixed object. Significant hydrostatic pressure builds up between the film and the surface of the blood. This may cause sufficient local distension of the film to disrupt the film resistance to a passage of blood through the film. As a further example, a ski glove constructed of a laminated fabric which includes an inner layer of breathable film may be worn by a skier who is squeezing a snow covered ski pole. Unless the film is supported by a layer of fabric, the hydrostatic pressure of melted snow against the film might cause excessive distension and rupture of the film, and the skier's hand would get wet. A similar result is obtained in the situation wherein the skier is wearing a laminated ski suit, one of the inner layers being a breathable film or membrane. If the skier sits on an ice covered seat of a ski lift, water of melted ice would pass through the outer layers of the garment and create significant hydrostatic pressure against the film. If the film is unsupported by other layers of the garment, there may be a resulting bowing of the film which impairs resistance of the film to liquid transport, and the skier gets wet.

One approach to overcoming the foregoing problems for use of the plastic film material in a surgical gown or drape is disclosed in Molde, U.S. Pat. No. 4,433,026 which discloses (column 3) a cloth-like material comprising a three-layer flexible laminate having a middle layer of plastic film material and two outer layers of plastic fabric materials secured to opposite sides of the middle layer by suitable adhesive means. The middle layer is substantially waterproof and air breathable while one of the outer layers is substantially dimensionally stable and the other outer layer is substantially dimensionally unstable to permit conformance of the fabric to the body of a person wearing the gown made from the fabric. Both the stable layer and the unstable layer are formed from polyester continuous filament yarn wherein, in the dimensionally stable layer, the yarn is woven in a poplin or regular broadcloth weave, while in the dimensionally unstable layer, the yarn is produced as a knit, such as a tricot knit. The resulting gown is reusable, and is rendered free of bacteria after each use cycle by a steam autoclaving of the gown. First, it is clear from the description in Molde, that the Molde gown is a relatively heavy and permanent gown, not intended for throw-away after a single use. A further example of a laminated moisture permeable sheet is given by Watabe, U.S. Pat. No. 4,507,356, wherein a woven or knitted fabric of nylon or polyester, such as nylon stocking material or gauze, serves as reinforcing material for plural layers of moisture-permeable plastic material. In the Watabe laminate, the gauze is treated with an epoxy resin to provide a base for the anchoring of hair in a wig.

However, in many hospitals, it is the practice to employ surgical gowns only once, and after their use to discard the gowns. In such application, is desirable to fabricate the gowns of a thin light-weight fabric to facilitate storage and transport of the gowns. Also, in the use of throw-away gowns, it is desirable to minimize the cost of the gowns. The use of multiple-layer fabrics in conjunction with a breathable film or membrane increases the cost significantly over that of the membrane itself. For the foregoing reasons, the laminated material of Molde would be contraindicated in a hospital procedure requiring a single use of surgical gowns followed by their discard. Furthermore, the use of the woven stocking material or gauze of Watabe provides very fine spacing between the yarns which, in combination with an applied coating of an epoxy or adhesive for attachment to the film, provides a significant reduction in the breathability of the resulting laminate as compared to a breathability of such a film without the woven material.

It is noted also that the foregoing use of the breathable film or membrane in the surgical gown or other garments is provided by way of example, and that there are other uses of such membranes such as in construction and industrial processes wherein a minimization of weight, thickness, and cost, and improved resistance to hydraulic pressure are advantageous.

SUMMARY OF THE INVENTION

The aforementioned problems are overcome and other advantages are provided by a membrane of breathable material and a method of constructing a fabric having the membrane, wherein the membrane is resistive to transport of a liquid, particularly water and human body fluids, and wherein, in accordance with the invention, the membrane is stabilized dimensionally by a reinforcing nonwoven matrix or grid of filaments in intimate contact with the breathable material. The filaments extend in plural directions within a two-dimensional geometric pattern across a layer of the breathable material to inhibit a distension of the membrane in any of the plural directions by any external forces which may be applied to the membrane. Furthermore, the arrangement of the filaments produces an array of cells as in a net or a veil, as is described below, this arrangement of the filaments enabling the reinforcing matrix or grid to resist the forces of any hydrostatic pressure which may be applied to the membrane, thereby to prevent excessive bowing and subsequent impairment of the membrane. In the general case, the forces applied to the membrane may be referred to as a force field which includes any one or plurality of the external forces and any one or plurality of forces resulting from the hydrostatic pressure.

The membrane may comprise a single film of plastic breathable material in accordance with a first aspect of the invention, or may comprise a composite structure of a layer of breathable material having regions of the breathable material interlaced with fibers, such as cellulosic fibers, in accordance with a second aspect of the invention. By way of example in construction of the membrane, the membrane may be formed by extrusion of a thin film of the breathable material. Alternatively, in a construction of the membrane as the composite structure of breathable material interlaced with the fibers, the breathable material may be extruded, coated or sprayed onto a carrier sheet composed typically of cellulosic fibers, such as a sheet of tissue paper which serves as a substrate to facilitate support and handling of the layer of breathable material. The breathable material, while still in liquid form, flows around the individual fibers and envelops the fibers. Thereafter, the breathable material hardens to form a membrane having the composite structure of the regions of the breathable material interlaced with the fibers.

The filaments of the reinforcing matrix are secured to the breathable material in a first aspect of the invention by a coating of adhesive upon the individual filaments. The adhesive bonds the filaments to a layer of the breathable material. The methodology of the invention permits an attachment of a further optional layer of nonwoven material by use of the same adhesive coating on the filaments of the matrix. The layers of the breathable material and the nonwoven material are essentially free of the adhesive because locations of the adhesive upon the layers of the breathable material and the nonwoven material are found only at the locations of the filaments of the matrix. This constitutes an open cell pattern of adhesive upon the layer of breathable material and the layer of nonwoven material. In a second aspect of the invention, the filaments of the reinforcing matrix are secured to the breathable material by embedding the filaments within the breathable material. In both aspects of the invention, the matrix of filaments is sufficiently pliable to insure that the resulting reinforced membrane drapes readily in the manner of a soft fabric of a garment.

In accordance with the invention, the filaments are arranged as a first planar array of substantially parallel filaments and at least a second planar array of substantially parallel filaments which intersect the filaments of the first array to form a system of cells. In a preferred embodiment of the invention, a minimum diameter, or cross-sectional dimension, of an individual one of the cells is greater by at least an order of magnitude (approximately a factor of ten) than a diameter of one of the filaments forming a boundary of the individual cell. This provides a matrix of wide open cells which is advantageous for reducing overall weight and thickness of the reinforced membrane, and for insuring that the filaments do not block any significant amount of the breathing passages of the breathable material. Furthermore, the open-cell configuration is advantageous for insuring that any adhesive coating, such as that noted above, employed for securing the filaments to the layer of breathable material does not ooze onto any significantly large region of the layer of breathable material, thereby to avoid any significant clogging of breathing passages of the breathable material. Preferably, the area of blockage of the breathable material by the filaments and/or the adhesive is smaller than the unblocked area.

The open-celled pattern of adhesive on the layer of breathable material reduces the blockage of breathing passages to such an extent that a non-breathable adhesive may be employed in the reinforcing of the membrane without significant reduction in the breathability of the membrane. This permits a manner of construction of the reinforced membrane wherein the matrix is constructed concurrently with the reinforcing of the membrane. In this method of construction, the first planar array of parallel filaments is provided, and the second planar array of filaments is laid thereon angled relative to the first array. Thereupon, adhesive is applied to the filaments to form a coating thereon, and the layer of breathable material is placed upon the filaments. The adhesive is operative to secure filaments of the first array to filaments of the second array, and to secure filaments of both arrays to the layer of breathable material.

The resulting reinforced membrane has substantially the same density, in terms of grams per square meter, as does the membrane without the reinforcing filamentary matrix. This accomplishes an object of the invention for retaining light weight in any covering, or object of apparel, produced from the membrane. Furthermore, in the reinforced membrane, the matrix of filaments introduces a resistance to curling of the membrane upon itself, and thereby facilitates a handling of the membrane. The improved handling is a considerable advantage in any further manufacturing processes involving the assembly of garments from the membrane. Also, if desired, the reinforced membrane may be provided with a thin coating layer of a nonwoven fabric for providing additional comfort to a person wearing a garment fabricated of the membrane. Such a thin nonwoven fabric layer would be significantly thinner and lighter than woven or knitted material which has been employed heretofore, thereby to retain the advantage of the invention of providing a lightweight and compact structure to a surgical drape or gown, suitable for any one time use followed by a discarding of the garment or drape.

It is useful also, in certain situations, to construct the grid filaments in elastic form, but wherein the elasticity of each filament is limited for a maximum amount of extension so as to avoid any rupture of the breathable film. The extension limits may be the same or may differ among the various filaments.

BRIEF DESCRIPTION OF THE DRAWING

The aforementioned aspects and other features of the invention are explained in the following description, taken in connection with the accompanying drawing figures wherein.

Identically labeled elements appearing in different ones of the figures refer to the same element in the different figures.

DETAILED DESCRIPTION

Figure 1:
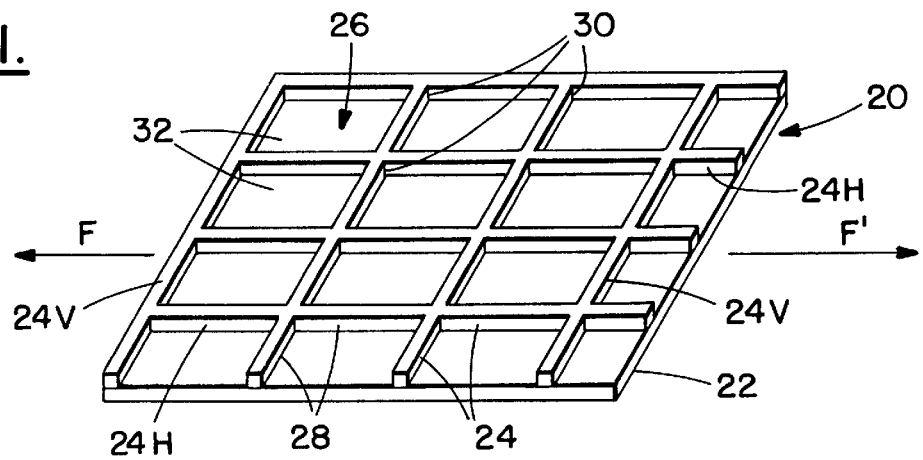
FIG. 1 is a stylized perspective view of a membrane of the invention having a film of breathable material reinforced by a matrix of filaments arranged in the form of a grid disposed along along a surface of the film, the figure showing also a reinforcing of the membrane via the grid against external forces.

FIG. 1 shows a layer of membrane 20 constructed in accordance with the invention and having a film 22 of breathable material reinforced by a matrix of filaments 24 disposed on a surface of the film 22. The filaments 24 are arranged in the form of a square grid 26 which is portrayed in a generic form understood to represent various forms of construction of the grid 26. An interface 28 between the grid 26 and the film 22 provides a means of securing the grid 26 to the film 22 such as by an adhesive or by a fusing of the material of the grid 26 to the film 22. Some of the filaments 24, indicated as filaments 24H, extend in a horizontal direction, and the remainder of the filaments 24, indicated as filaments 24V, extend in a vertical direction to intersect at junctions 30 with the formation of grid cells 32. The terms horizontal and vertical are in reference to the portrayal of the membrane 20 in FIG. 1, and do not refer to a specific orientation of the membrane 20 which can have any orientation. By way of example in the construction of the grid 26, the horizontal filaments 24H may overlie the vertical filaments 24V at the junctions 30, and may be connected at their respective junctions 30 by an adhesive or by fusion. Alternatively, the entire grid 26 may be formed by a stamping process or a masking process.

The film 22 may be constructed of a water vapor permeable polyurethane or acrylate copolymer, or urethane and urethane copolymers as well as modified polyolefin or other polymeric material that can be so fashioned to be microporous, and also of a polymer constructed of hard and soft resin segments. The film 22 is transparent and has sufficient elasticity, and particularly drape, to be conformable to contours of a human body as well as an animal body. Typically, the film 22 has a thickness in a range of approximately 1–3 mils, though film thicknesses in the order of 0.3–10 mils may be considered. A moisture vapor transport rate (MVTR) in access of approximately 250 grams per square meter per 24 hour interval at a relative humidity of 50%, as measured by ASTM method E96B, is desired in a situation wherein the film 22 may be placed directly on a person's skin. In such a case the MVTR insures that the skin can breathe properly in the sense that water vapor discharged through the skin can permeate through the film 22 to be evaporated in air. Further details in the construction of a moisture vapor transmitting elastomeric film is disclosed in Metcalfe et al, U.S. Pat. No. 4,596,738 issued Jun. 24, 1986. Moisture-vapor-permeable pressure-sensitive adhesive material is disclosed in Hodgson, U.S. Pat. No. 3,645,835 issued Feb. 29, 1972 and reissued as Re. 31,886, on May 14, 1985. Such a moisture vapor permeable adhesive may be employed at the interface 28 for securing the grid 26 to the film 22.

The filaments 24 may be made of vegetable fibers or of plastic material such as polyethylene, polyurethane, polypropylene, polyamide, polyester, nylon or fiberglass, and have a thickness of typically 5 mils as is employed in the manufacture of scrim. It is noted that the term scrim as used in textile manufacture encompasses a wide variety of filamentary structures including loosely laying filaments wherein cohesion among the filaments is attained by adhesion due to air holes in the filaments. Such loosely laying scrims are not employed in the practice of the invention but, rather, the filaments 24 of the grid 26 are secured to each other at the junctions 30 between contiguous one of the filaments 24. A suitable form of scrim for the practice of the invention is manufactured by Cowed Plastics of Minneapolis, Minn. under the name of CONNECT. This construction of the grid 26 provides sufficient dimensional stability to enable the grid to provide dimensional stability to the membrane 20. Furthermore, the securing of the grid 26 to the film 22 provides still further dimensional stability wherein the film 22 inhibits distortion of any of the grid cells 32. The extensions of the individual filaments 24 linearly in the horizontal and in the vertical directions enables the filaments 24 to resist any external tensile forces such as the forces F and F' which may be applied to the membrane 20. Thus the composite structure of grid 26 and film 22 is stronger than either the grid 26 or the film 22 by itself, and gives to the membrane 20 a significant improvement in dimensional stability.

Figure 2:
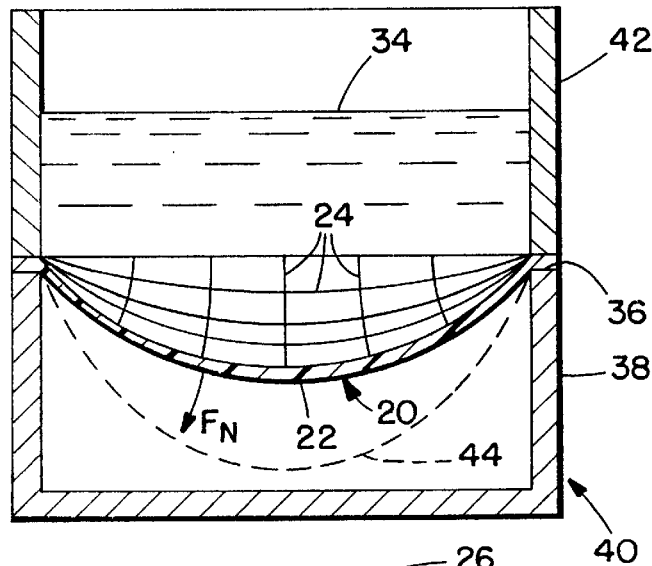
FIG. 2 demonstrates resistance to distension of the membrane of FIG. 1 under the influence of a hydrostatic pressure.

With reference to FIGS. 1 and 2, the dimensional stability may be explained with reference to a force field. In FIG. 1, the force field is represented by the force vectors F and F' pulling in opposite directions along horizontal ones of filaments 24. In FIG. 2, the force field is represented by a normal force Fn extending in a direction normal to a surface of the membrane 20 in response to a hydrostatic pressure which may be developed, by way of example, by a column of liquid 34. FIG. 2 is provided to demonstrate the strength of the membrane in is capacity to resist hydrostatic pressure. In FIG. 2, the membrane 20 is draped over the top edge 36 of a sidewall 38 of a beaker 40 having a right circular cylindrical shape. To simplify the drawing, the filaments 24 are shown diagrammatically. A cylindrical section of pipe 42 is placed above the sidewall 38 to clamp a peripheral edge region of the membrane 20 in place between the sidewall 38 and the pipe 42. The liquid 34, which may be water, is loaded into the pipe 42 resulting is a distension of the membrane from an initial attitude which is substantially planar to a bowed attitude which is shown in FIG. 2. The filaments 24 restrain the film 22 from further distension, such as that indicated by the dashed line 44, which would occur in the absence of the filaments 24.

If sufficient hydrostatic pressure be present, the distension of the film 22 in the absence of the reinforcing filaments 24, would be great enough to rupture the film 22. The demonstration of FIG. 2 is similar to the Mullens test for textiles. A similar test for protective membranes, ASTM ES 21, 22 conducted with a beaker diameter of three inches shows that the membrane 20, constructed in accordance with the invention with the breathable film 22 and the matrix of reinforcing filaments 24, is able to withstand a hydrostatic pressure of 2 psi (pounds per square inch). This shows that the membrane 20 can be used safely in critical situations, such as the use of the membrane 20 in the construction of a surgical gown for protection of a physician from body fluids, without any significant danger of rupture or other failure of the membrane 20. It has been demonstrated that the identical membrane without scrim as a test backing will rupture or distort. Distortion of the cells within the membrane, or channels within a monolithic structure, can cause elongation or deformation enabling viral pathogens to pass through the elongated openings of such cells or channels.

Figure 3:
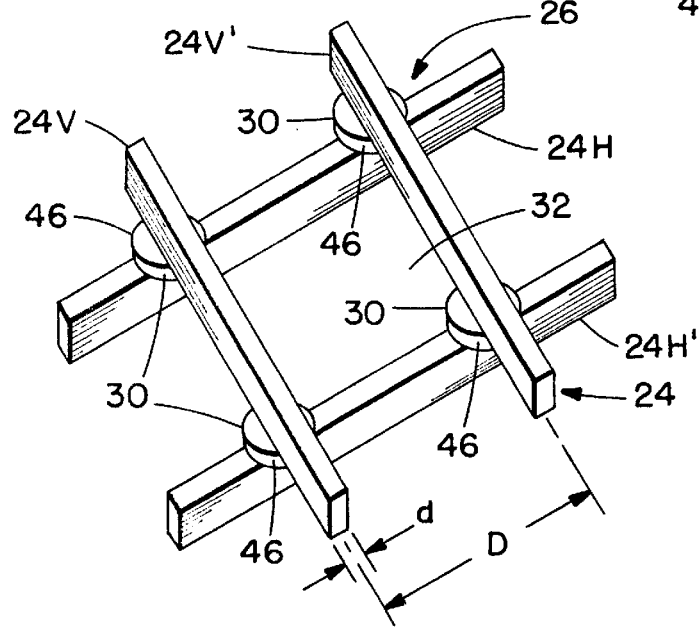
FIG. 3 is a stylized fragmentary view of the grid of FIG. 1.

FIG. 3 is a fragmentary stylized view of the grid 26 showing four of the filaments 24 which are identified further as two horizontal filaments 24H and 24H' intersecting with two vertical filaments 24V and 24V' via junctions 30 located at the four corners of the square gird cell 32. The filaments 24 are shown in the form of rigid straight beams with rectangular cross section to facilitate a showing of their interconnection, it being understood that, in practice, the filaments 24 may have a generally circular cross section, and that the filaments bend so as to contact the film 22 (FIG. 1). Each of the junctions 30 include a disk 46 of adhesive for securing the respective filaments, such as the filament 24V to the filament 24H. Alternatively, the disk 46 may be of plastic material to represent a fusion of the plastic material of the filament 24V to the plastic material of the filament 24H.

A feature of the invention is the relatively wide spacing between the filaments 24, such as the spacing between the filaments 24V and 24V', and the spacing between the filaments 24H and 24H', which form boundaries of the cell 32. The cell 32 is presumed, by way of example, to be square; however, the cell 32 may be rectangular if desired. The construction of the grid 26 may be referred to as open-cell construction because the distance on centers, D, between centerlines of the filaments 24 is at least approximately an order of magnitude (a factor of ten) greater than a diameter, d, of a filament 24. This is important for insuring that the grid 26 does not impede the breathability of the film 22 (as shown in FIG. 1). Furthermore, in the event that the grid 26 is to be secured to the film at the interface 28 (FIG. 1) by an adhesive, then the adhesive can be applied to the filaments 24 of the gird 26 without a need for covering the entire film 22 with the adhesive, this sparing use of adhesive enhancing the breathability of the membrane 20 (FIG. 1). In accordance with a feature of the invention, in the situation wherein the adhesive is applied only to the filaments 24 of the grid 26, as by an adhesive coating of the filaments, there is no requirement that the adhesive be a breathable adhesive since the open cell construction of the grid 26 ensures breathability of the membrane 20.

Figure 4:
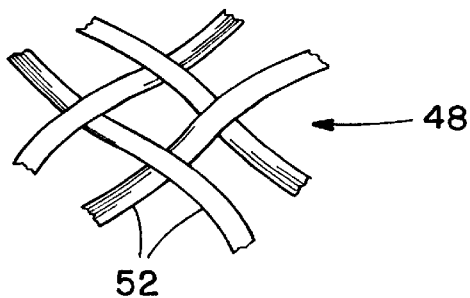
FIG. 4 is a stylized fragmentary view of a knitted fabric.
Figure 5:
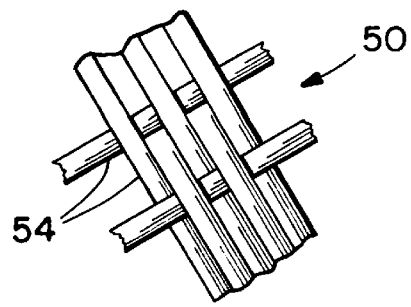
FIG. 5 is a fragmentary plan view of a woven fabric.

The rigid securing of the filaments 24 at the respective junctions 30 permits the open-cell construction of the grid 26, and is a source of strength to the grid 26. This may be appreciated from a viewing of a fragmentary portion of a knitted fabric 48 in FIG. 4 and a viewing of a fragmentary portion of a woven fabric 50 in FIG. 5. In both the knitted and the woven fabrics, the threads 52 (FIG. 4) and the threads 54 (FIG. 5) rely on rigidity of the threads and frictional contact among the threads to hold the respective fabrics together. The resulting interlocking of the threads can be maintained only in the situation wherein the spacing between threads is relatively small, ranging from actual contact in the close weave of FIG. 5 to a spacing not much greater than approximately a diameter of a thread. Furthermore, in the fabrics 48 and 50, such cells as may be formed between the threads are not permanent, but are subject to alteration by a sliding of one thread upon another.

Figure 6:
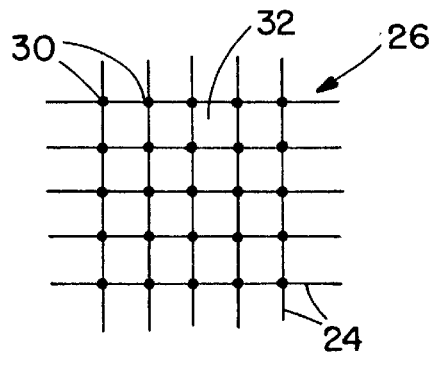
FIG. 6 is a diagrammatic representation of the grid of FIG. 1 wherein each cell has the shape of a square.
Figure 7:
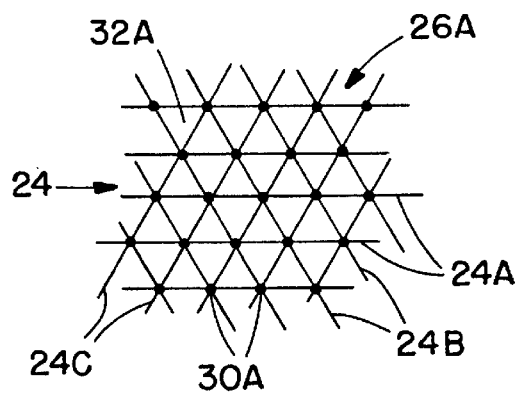
FIG. 7 is a diagrammatic view of an alternative embodiment of the grid wherein each cell has the shape of an equilateral triangle.

FIGS. 6 and 7 demonstrate two different configurations of grid for construction of the reinforcing matrix of filaments for the breathable membrane, in accordance with the invention. Each figure show a two-dimensional geometric pattern of the filaments 24. FIG. 6 shows diagrammatically the grid 26 of FIG. 1 with cells 32 formed with a square shape by intersection of horizontal and vertical filaments 24 at junctions 30. If desired, the grid 26 may be replaced by a grid 26A shown in FIG. 7 wherein the filaments 24 are arranged in three groups, namely, a group of filaments 24A, a group of filaments 24B and a group of filaments 24C which intersect at junctions 30A at angles of 60 degrees. Each of the resulting cells 32A has the shape of an equilateral triangle. The six cells 32A surrounding a single one of the junctions 30A define a hexagon.

Figure 8:
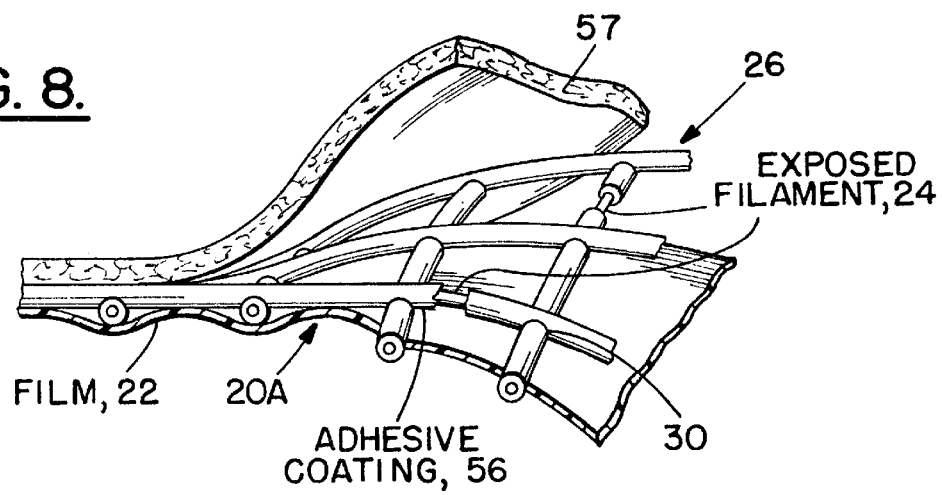
FIG. 8 is a side elevation view, partially disassembled, of a portion of a laminated fabric incorporating the membrane of FIG. 1 wherein the grid is coated with an adhesive which secures the grid to the film, as well as to a layer of nonwoven material.

FIG. 8 shows an embodiment of membrane 20A wherein an adhesive coating 56 coats all of the filaments 24 of the grid 26 and which, upon contact with the film 22 and upon application of heat to activate the adhesive, secures the film 22 to the grid 26. A nonwoven layer 57 of carded material, such as carded cotton or carded polyester, may be secured to the membrane 20A if desired to provide a laminated fabric having the fluffy feel of the carded material. In accordance with a feature of the invention, the nonwoven layer 57 is secured to the grid 26 by means of the adhesive of the coating 56, in the same fashion as the securing of the film 22 to the grid 26. In the right side of the figure, the three layers of the fabric, namely, the film 22 and the grid 26 and the nonwoven layer 57, have been pulled apart and have been twisted around to facilitate a viewing of the three layers. Also, portions of the coating 56 are are cut away to expose the underlying filaments 24, thereby to facilitate a viewing of the construction of the membrane 20A. The adhesive of the coating 56 also aids in securing the vertical and the horizontal filaments 54 at their respective junctions 30.

Figure 9:
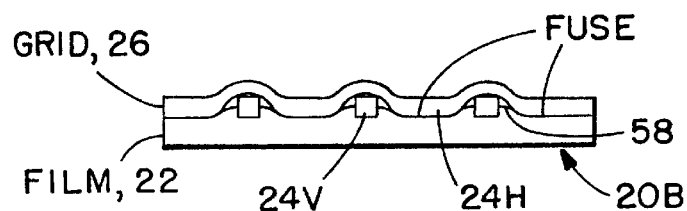
FIG. 9 is a diagrammatic side elevational view of a portion of the membrane of FIG. 1 wherein the grid is secured to the film by fusing.

FIG. 9 shows an embodiment of membrane 20B wherein the grid 26 is fused to the film 22. The representation of the membrane 20B in FIG. 9 is somewhat diagrammatic, and shows a horizontal filament such as the filament 24H, looping over vertical filaments, such as the filament 24V at a junction 30. Locations of fusing are indicated, by way of example, at 58.

Figure 10:
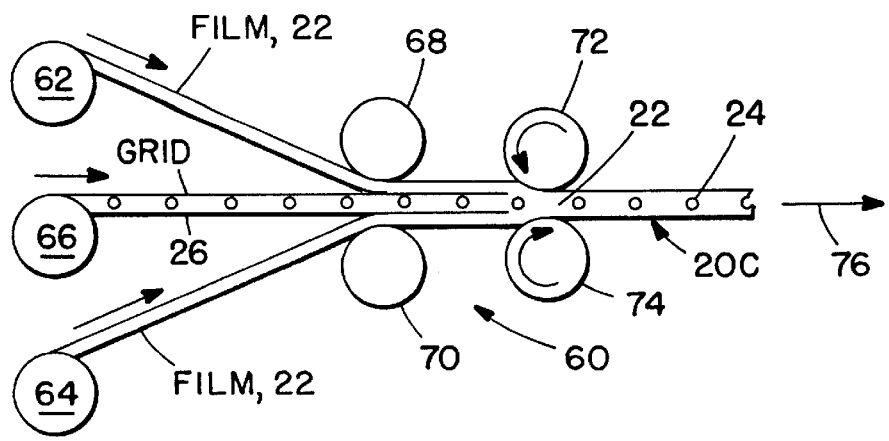
FIG. 10 shows diagrammatically an apparatus for constructing an embodiment of the membrane wherein the grid is embedded within breathable material of the film.

FIG. 10 shows construction of a further embodiment of membrane 20C wherein the grid 26 is embedded within the breathable material of the film 22, rather than being secured to a surface of the film 22 as demonstrated in FIGS. 8 and 9. In FIG. 10, an apparatus 60 for forming a membrane comprises an upper feed roll 62 for feeding an upper layer of film 22, a lower feed roll 64 for feeding a lower layer of film 22, and a central feed roll 66 disposed between the rolls 62 and 64 for feeding the grid 26. Heated guide rolls 68 and 70 bring the upper and lower layers of the film 22 into contact respectively with upper and lower surfaces of the grid 26. Heat from the rolls 68 and 70 is conducted into the layers of film 22 to induce a partial melting of film and a fusing of the films to the upper and the lower surfaces of the grid 26. Heated pressure rolls 72 and 74 force the partially melted material of the films 22 into the spaces between the filaments 24 of the grid 26 to form the composite structure of the membrane 20C wherein the filaments 24 are embedded within the breathable material of the films 22. The apparatus 60 is provided by way of example to demonstrate a method of continuous production of a layer of the membrane 20C, the layer of the membrane 20C exiting from the pressure rolls 72 and 74 in the direction of an arrow 76.

Figure 11:
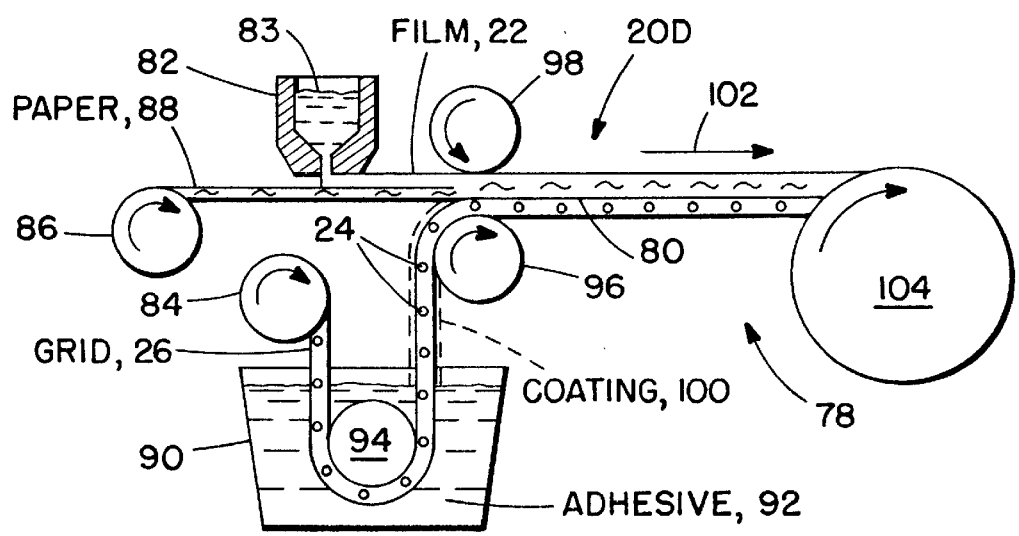
FIG. 11 shows diagrammatically an apparatus for producing further embodiments of the membrane wherein fibers of a paper become embedded within the breathable material of the film, and wherein an adhesive is used for securing the grid to the film to attain the reinforcing of the membrane.

FIG. 11 shows apparatus 78 for forming a layer of an embodiment of membrane 20D wherein a layer of film 22 is impregnated by fibers 80, such as cellulosic fibers, and is in contact with the grid 26. The apparatus 78 comprises an extruder 82 of a breathable resin 83 for forming the film 22, a lower feed roll 84 for supplying the grid 26, and an upper feed roll 86 for feeding a layer of the fibers 80 in the form of a tissue paper 88. A trough 90 of liquid adhesive 92 is provided with a guide roll 94 for conducting the grid 26 from the feed roll 84 through the adhesive 92 to a further guide roll 96. The apparatus 78 further comprises a guide roll 98 facing the guide roll 96, both of the guide rolls 96 and 98 being heated. In operation, as the grid 26 passes through the trough 90, the grid 26 becomes covered with the adhesive 92 in the form of a coating 100. Upon rotation of the feed rolls 86 and 84, the paper 88 and the grid 26 with its adhesive coating 100 are feed between the two heated guide rolls 96 and 98. The span of the paper 88 between the rolls 86 and 96 serves as a support for receiving the resin 83 as it exits the extruder 82. Upon contact with the paper 88, the resin 83 envelops the fibers 80 of the paper 88 and cures to form film 22A with the fibers 80 embedded therein. The heat provided by the rolls 96 and 98 is operative also to activate the adhesive of the coating 100 to secure the grid 26 to the film 22A. The laminated assembly exiting the rolls 96 and 98 thus constitutes the membrane 20D which comprises the layer of film 22A wherein the fibers 80 are embedded therein, and wherein the film 22A is reinforced by the grid 26. Direction of movement of the component layers of the membrane 20D is indicated by arrows such as the arrow 102. The membrane 20D is wound on a take-up roll 104. The adhesive of the coating 100 may be a breathable adhesive, but breathability is not required because the layer of adhesive 100 is found only on the filaments 24 of the grid 26 and therefore offers no significant blockage of the film 22 in view of the open-cell construction of the grid 26.

Figure 12:
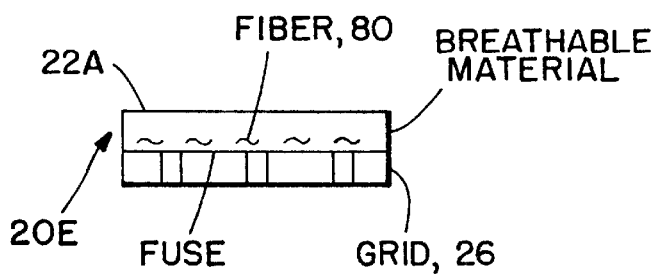
FIG. 12 shows diagrammatically a side elevation view of an alternative embodiment of membrane produced by the apparatus of FIG. 11 wherein the securing by adhesive is replaced with a securing by fusion.

FIG. 12 show a further embodiment of membrane 20E which is produced by the apparatus 78 of FIG. 11 wherein the adhesive 100 is eliminated and the grid 26 is secured by fusion to the breathable material in the layer 22A. Such fusing requires that the grid 26 be fabricated of a plastic having a melting temperature lower than that of the breathable material of the film 22A. The fibers 80 are substantially encased by the breathable material of the film 22A.

Figure 13:
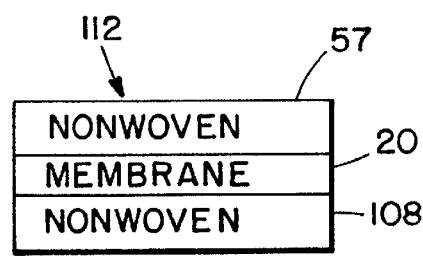
FIG. 13 shows diagrammatically the construction of a textile fabric by securing a nonwoven fabric to one or more surfaces of the membrane of FIG. 1.

FIG. 13 shows diagrammatically that, in the use of the membrane 20 for textiles, it may be advantageous to provide for a layer of nonwoven material 108 secured by a breathable adhesive (not shown) to the bottom surface of the membrane 20. Alternatively, the layer 57 of nonwoven material may be secured to a top surface of the membrane 20 by the adhesive coating on the filaments 24 of the grid 26, as described above with reference to FIG. 8. In the situation wherein only the layer 57 is to be applied to the top surface of the membrane 20 via the adhesive coating of the grid 26, there is no requirement that the adhesive be breathable because of the open cell construction of the grid 26. Also, if desired, both of the layers 108 and 57 of the nonwoven material may be applied to the opposite surfaces of the membrane 20. The composite structure of the membrane 20 with the two layers 108 and 57 of the nonwoven material constitutes a textile fabric 112. While the fabric 112 is described in terms of the generic form of membrane 20, disclosed hereinabove with reference to FIG. 1, it is noted that the membrane 20 of the fabric 112 may be constructed in accordance with any one of the embodiments of membrane 20A–E as described hereinabove. It is to be emphasized that the use of the nonwoven layers 108 and 57 is to provide a comfortable feel or hand to the fabric 112, and that the membrane 20, by itself, provides suitable strength and breathability for use in the fabrication of a garment, a surgical drape, a wall covering, or an element in industrial apparatus.

The nonwoven material of the fabric 112 is particularly advantageous over woven material because the nonwoven material can be constructed in a form which is exceedingly thin for a protective layer, typical thicknesses of the layers 108 and 57 being in the range of approximately 1–30 mils. A typical value of the thickness is approximately 10 mils. In accordance with a feature of the invention, the nonwoven material of the fabric 112 is not required to have any tensile strength because the grid 26 (FIGS. 1 and 8) of the membrane 20 provides the necessary tensile strength for the fabric 112. Thus, by way of example, the nonwoven material may be the aforementioned carded material, such as a carded cotton or a carded polyester, which provides wearer comfort but lacks tensile strength in a direction transverse to the direction of the carding. In the carded material, there are adequate voids to allow for the evaporation of water vapor from a surface of the membrane 20. In the case of the construction of a throw-away surgical gown, a layer of nonwoven material is preferred to a layer of knitted material because the latter has much greater bulk which would render the gowns inconvenient for storage.

Figure 14:
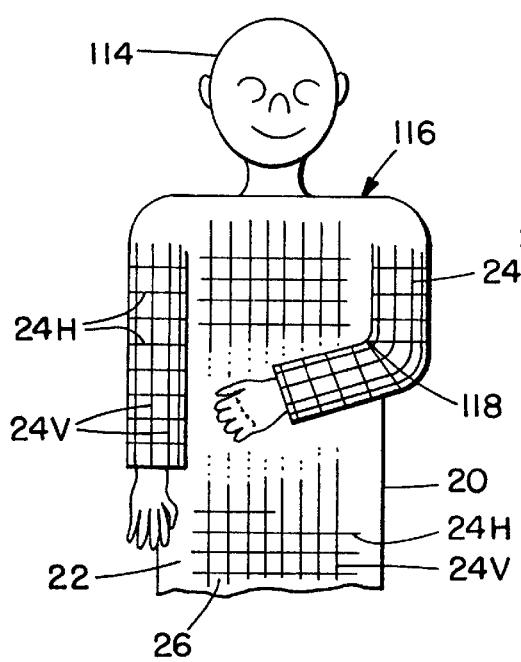
FIG. 14 shows a stylized view of a person wearing a surgical gown constructed with the membrane of FIG. 1.

FIG. 14 shows a person 114 wearing a gown 116 constructed of the membrane 20 wherein the membrane 20 may be formed in accordance with any of the embodiments 20A–E described hereinabove. To facilitate the description of the gown 116, it is presumed that neither of the nonwoven layers 108 and 110 of FIG. 13 are employed on the gown 116 of FIG. 14. However. it is to be understood that either one or both of the layers 108 or 57 may be employed in the construction of the gown 116, if desired. The grid 26 of the membrane 20 is shown diagrammatically in FIG. 14 with individual ones of the vertical filaments 24V and the horizontal filaments 24H being indicated.

It is noted that the mutual reinforcement between the grid 26 and the film 22 provides sufficient strength and dimensional stability to the membrane 20 such that the filaments 24 may be oriented in any desired direction relative to the body of the person 114. This includes sufficient dimensional stability to resist distension at the person's elbow 118 during a bending of the elbow 118, by way of example. However, for maximum resistance to distension of the membrane 20 due to a bending of the elbow 118, it is advantageous to have the filaments 24V oriented in a direction parallel to the direction of the applied force field, this being parallel to the axis of the person's arm. In similar fashion, for maximum resistance to distension occurring upon a bending of the person's back, it is advantageous to have the membrane 20 oriented, in the region of the person's back, with the filaments 24V oriented in a direction parallel to the person's spine. Also, it is noted that the grid 26 employed in the fabrication of the gown 116 may be replaced with the grid 26A (disclosed in FIG. 7) if desired. With either grid, the deployment of the filaments in directions parallel to the axis of the arm and to the spine have the person 114 provides for a maximum resistance to distension due to bending.

Figure 15:
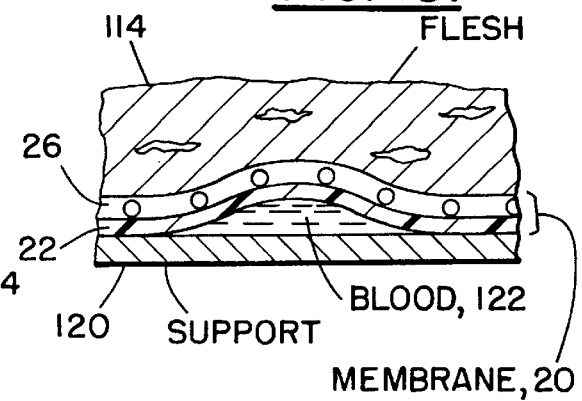
FIG. 15 is a sectional view, partly stylized, showing the envelopment of a puddle of blood by the fabric of the gown of FIG. 14 in a situation wherein the person of FIG. 14 leans against the support.

FIG. 15 shows how the resistance to hydrostatic pressure, discussed above with reference to FIG. 2, is useful in explaining how the membrane 20 of the gown 116 of FIG. 14 can resist the intrusion of body liquids which may have spilt on furniture within an operating room. By way of example, consider a support, such as the top of a table 120 in the situation wherein the person 114 places his arm on the table 120. In the event that there is a puddle 122 of blood on the table 120, only the membrane 20 separates the flesh of the person 114 from the blood. The force of the arm on the table 120 can produce a significant amount of hydrostatic pressure upon the blood puddle 122 such that, in the event a non-reinforced breathable film were employed in the gown 116, there would be a danger that a resulting localized distension of such film might result in a rupture or failure of the film at the site of the blood with a possible hazard of contamination. However, by virtue of the increased strength and dimensional stability afforded by the invention in the use of the reinforcing grid 26 in combination with the breathable film 22 to provide for the reinforced membrane 20, the gown 116 can be used safely within the operating theater to prevent contamination by spilt body fluids.

Figure 16:
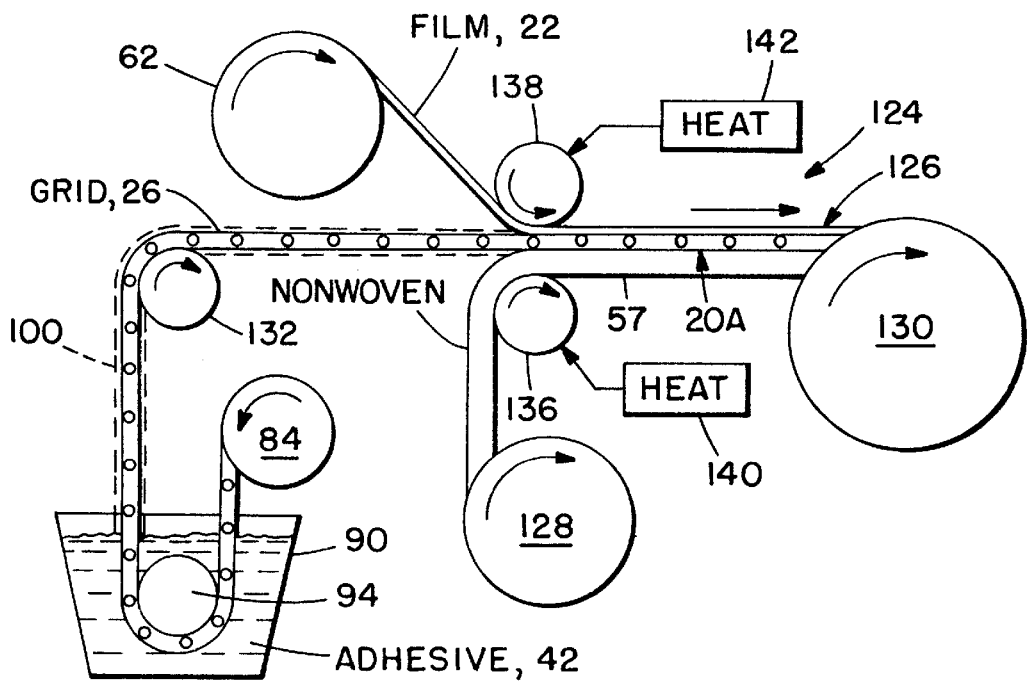
FIG. 16 is a diagram of apparatus used in the practice of the methodology of the invention for assembling a laminated fabric including a reinforced membrane of breathable material.

FIG. 16 presents apparatus 124 which demonstrates a feature of the invention wherein the adhesive coating 100 on the grid 26 can be used simultaneously in the fabrication of a laminated fabric 126, such as that of FIG. 8, having both a reinforced breathable membrane 20A and the layer 57 of nonwoven material. If desired a woven material may be substituted for the nonwoven material of the layer 57. For supplying the grid 26 and its adhesive coating 100, the apparatus 124 comprises components previously described with reference to the apparatus 78 of FIG. 11, namely, the feed roll 84, the trough 90 containing the adhesive 92, and the guide roll 94 within the trough 90. The apparatus 124 further comprises a feed roll 128 providing the nonwoven material of the layer 57, a take-up roll 130 for receiving the fabric 126, and three guide rolls 132, 136 and 138. Also included in the apparatus 124 is the feed roll 62 of the film 22 previously described with reference to the apparatus 78 of FIG. 10. The rolls 136 and 138 are heated nip rolls wherein the roll 136 is heated by a source 140 of heat, and the roll 138 is heated by a source 142 of heat.

In operation, the grid 26 with its adhesive coating 100 is passed via the guide roll 132 to a location in the nip between the rolls 136 and 138. The film 22 is secured to the grid 26 by the adhesive of the coating 100 to provide the membrane 20A. The nonwoven layer 57 advances to the nip of the rolls 136 and 138 where heat and pressure unite the layer 57 with the grid 26 of the membrane 20A. The heat of the rolls 136 and 138 activates the adhesive of the coating 100 secure the nonwoven layer 57 to the grid 26 to form the fabric 126. The temperature of the rolls 136 and 138 is typically in a range of 180–250° F., this being lower than the melting temperature (300–500 degrees Fahrenheit) of the breathable resin. A suitable adhesive is a water-based adhesive PVA/EVA manufactured by H. P. Fuller. The completed fabric 126 is then wound on the roll 130.

Figure 17:
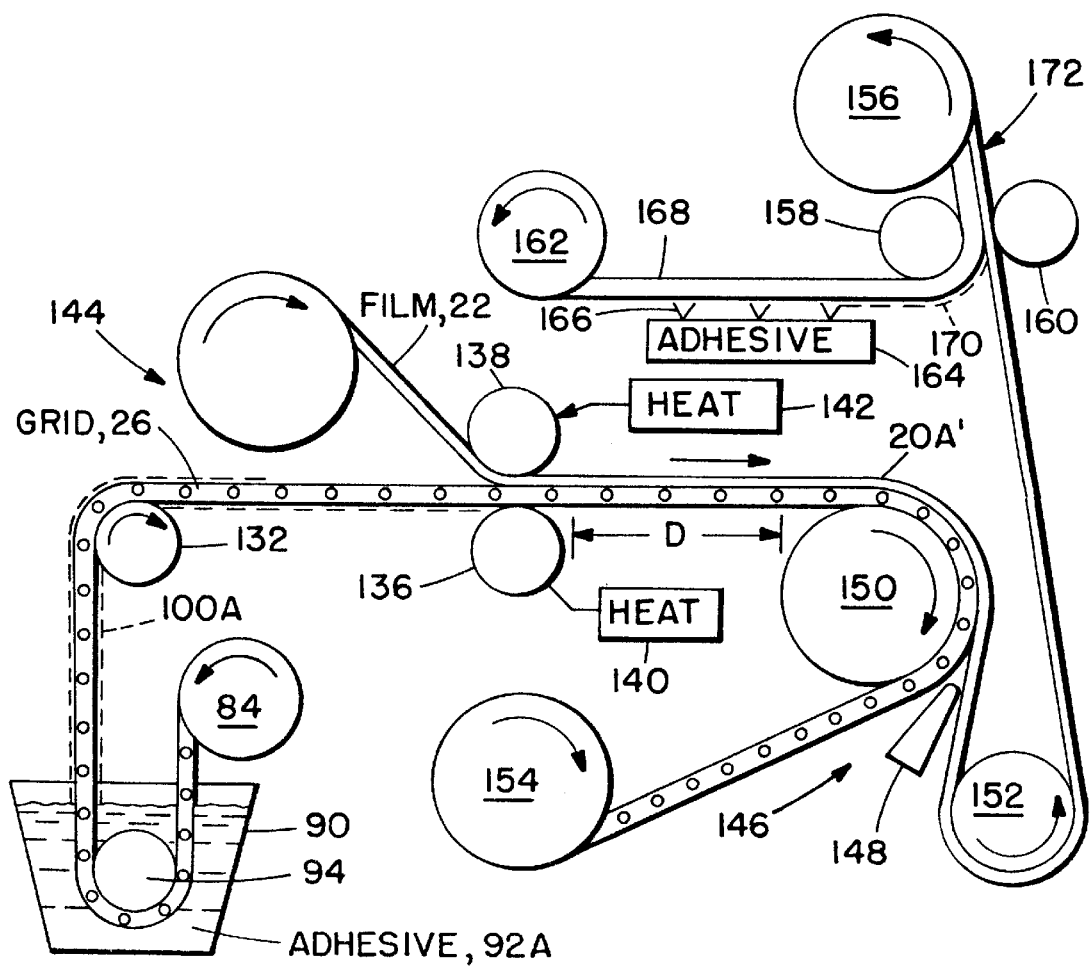
FIG. 17 is a diagram of apparatus for construction and utilization of a reinforced membrane formed with a relatively weak adhesive permitting a stripping off of a reinforcing grid for subsequent use of the membrane.

FIG. 17 shows apparatus 144 for construction and utilization of a temporarily reinforced membrane 20A' which has the same physical structure as the membrane 20A of FIG. 8 but differs therefrom in that the membrane 20A' has a substantially weaker adhesive which provides for a temporary adhesion between grid and membrane allowing the grid to be stripped off from the membrane for production of a further product from the membrane. The apparatus 144 includes all of the components of the apparatus 124 of FIG. 16, except for the rolls 128 and 130, and further comprises a stripping station 146 including a separation blade 148 and two guide rolls 150 and 152. Also included in the apparatus 144 are two take-up rolls 154 and 156, two heated guide rolls 158 and 160 which may be heated by means (not shown) such as the heat sources 140 and 142, a feed roll 162, and an adhesive station 164 outputting jets 166 of adhesive upon a surface of a fabric 168.

In the operation of the apparatus 144, the grid 26 is passed through a weak adhesive 92A in the trough 90 to coat the grid 90 with a coating 100A of the weak adhesive 92A. A suitably weak adhesive is obtained by diluting the aforementioned PVA/EVA adhesive with additional water, for example, by use of three or four times the normal amount of water. The film 22 is fed upon the grid 26 from the roll 62. The grid 26 with the film 22 thereon is passed between the heated rolls 136 and 138 to activate the weak adhesive for securing the film 22 temporarily to the grid 26, thereby to produce the reinforced membrane 20A'. The membrane 20A' then advances over the roll 150 of the stripping station 146 wherein the grid 26 is separated from the film 22 by the blade 148. The grid 26 is wound on the take-up roll 154. The film 22 passes via the roll 152 to the heated rolls 158 and 160. The fabric 168 is fed from the roll 162 to the adhesive station 164 which produces a coating 170 of adhesive upon the fabric 168. The fabric 168 then passes to the heated rolls 158 and 160 which press the fabric 168 against the film 22 as the heat of the rolls 158 and 160 activate the adhesive to laminate the film 22 to the fabric 168. The resulting laminate 172 outputted by the rolls 158 and 160 is wound on the take-up roll 156. The fabric 168 may be woven or nonwoven. As an example of a woven fabric, the fabric 168 may be a cotton polyester having an elongation less than approximately 40% when subjected to stretching so as not to exceed the stretching capability of the film 22, and thereby insure the integrity of the laminate 172.

In accordance with a feature of the invention, the temporary reinforcing of the film 22 in the form of the membrane 20A' represents a convenient method of transporting the film from one location to another location in a manufacturing process. This form of transportation takes advantage of the reinforcement of the grid 26 to protect the film 22 from excessive stretching and tearing, such as might occur during a possible situation of rough handling in a manufacturing facility. Such transportation is indicated schematically by the travel of the membrane 20A' through a distance D from the roll 136 to the roll 150. By way of further embodiment in this method of transporting a thin film in a manufacturing environment, it is noted that the roll 150 may be employed as a take-up roll upon which the membrane 20A' can be stored until required for the manufacturing process of laminating the film 22 to the woven fabric 168. Upon termination of the storage, the roll 150 would be placed in the stripping station 146 for feeding the membrane 20A' to the blade 148. It is noted also that the film 22 of FIG. 17 is understood to be representative of various forms of thin films and membranes such as the composite film 22A of FIG. 12.

In the foregoing description of the membrane 20 and its use as a reinforced fabric for construction of wearing apparel, the filaments 24 of the grid 26 have relatively little recoverable elastic strain, being relatively inelastic, as compared to the material of the film 22. The material of the film 22 has a maximum permissible limit of distension beyond which there is danger of a rupturing of the film. The relatively low elasticity of the filaments 24, as compared to the relatively high elasticity of the film 22, provides far greater dimensional stability to the grid 26 than is present in the film 22. This protects the film 22 from excessive distension so as to prevent rupture of the film 22. This is a very useful feature in the case of a loosely fitting garment, such as a surgical gown or drape, wherein a stretching or bending movement of a person wearing the garment produces significant stress on the membrane 20, which stress is counteracted by the grid 26 to prevent rupture of the film 22.

However, it is recognized that the breathable elastic material of the film 22 is useful also in the construction of tightly fitting garments such as swim wear, underwear, children training pants, and pants for incontinent persons, by way of example. Here, too, there is a danger of excessive stretching or distension of the film 22, as may be brought on by a person's bending or stretching movements, with the possibility of a rupturing of the film 22. Use of the grid 26 of square cells 32, or the grid 26A of triangular cells 32A, in the garment would provide the necessary protection of the film 22 but, due to the grid's relatively low elasticity, would impede movements of the person wearing the garment.

This limitation in the utility of the grid 26 is overcome, in accordance with a further feature of the invention, by constructing the grid filaments of an elastic material of limited stretch capability. Thus, stretching of a filament can occur to accommodate a movement of the wearer of the garment, but the capacity for stretching in the filament is strictly limited to a specific limit of extension, beyond which limit the filament strongly resists further extension. Suitable material for such construction of the filaments 24 is available commercially in the form of core spun thread. In core spun thread, a substantially inelastic outer thread is wound spirally around a core thread of elastic material. Stretching of the core spun thread is possible until the spiral inelastic thread becomes substantially straight, at which point the extension limit is reached, and no further extension occurs. For construction of the filament 24, the extension limit of the core spun thread is set at a value well below the elastic limit of the film 22, thereby to insure that the grid 26 prevents the film 22 from stretching to a point of rupture. Such a grid provides the dual benefits of sufficient dimensional stability of the membrane 20 for insuring integrity of the film 22 while allowing for bending and stretching movements of a person wearing a garment of the membrane. The depiction of the square cells of the grid 26 and the equilateral triangular cells of the grid 26A in FIGS. 6 and 7 are obtained for the case wherein the filaments are in their non-distended state.

By way of example in the construction of an elastic core thread of a core spun thread for the filament 24, the elastic core thread may be constructed of a polyether polyester resin such as that employed in a fabric available commercially under the name of Domique by Kimberly Clark. By way of further example, polyurethane may be employed for fabrication of an elastic core thread. Such a construction of the core thread may have a recoverable elastic strain at least double the unstrained length of the core thread. The spirally-wound relatively inelastic thread has a sufficiently high tensile strength to maintain integrity of the fabric, or membrane 20, and may be nylon, by way of example. The spirally-wound relatively inelastic thread may be provided, by way of example, with a length which limits the extension of the core thread to a factor of 1.5 times the unstrained length of the core thread, which factor is also the extension limit of the filament 24. Thereby, the elastic core thread is prevented from undergoing an extension which exceeds its elastic limit. For the present example, the film 22 may be constructed with an elastic limit equal to or greater than the elastic limit of the core thread so that the extension limit of the filament also prevents the film 22 from undergoing an extension beyond its elastic limit. The filaments 24, constructed of the core spun thread, may be adhered to the film 22 by adhesive or by fusion, by way of example.

By way of alternative embodiments of the grid 26 which comprises both the set of horizontal filaments 24H and the set of vertical filaments 24V, if desired, only one of the sets of filaments 24H or 24V may be constructed of the elastic material of limited stretch capability, while the other of the sets of the filaments 24V or 24H may be constructed of the relatively inelastic material. This provides dimensional stability to the membrane 20 in one direction while allowing for limited stretch in the transverse direction. The use of the limited stretch form of the filaments 24 may be employed also in the grid 26A of triangular cells. Alternatively, both sets of filaments may have limited stretch construction wherein the extension limit of the horizontal filaments 24H differs from the extension limit of the vertical filaments 24V. Such construction of the grid may be used also in the fabric of FIG. 8 wherein the grid 26 is disposed between the layer of the film 22 and the layer 57 of the nonwoven material.

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

What is claimed is:

1. A breathable membrane, resistive to transport of liquid water, and having limited distension in response to a force, the membrane comprising:

a layer of breathable material resistive to transport of liquid water; and a reinforcing matrix of filaments extending linearly in plural directions within a two-dimensional geometric pattern along said layer of breathable material to inhibit said distension;

wherein a first plurality of said filaments intersect a second plurality of said filaments to form cells within said matrix, a minimum cross-sectional dimension of an individual one of said cells being greater by at least approximately an order of magnitude than a diameter of one of said filaments to provide open areas of said layer of breathable material free from obstruction by said filaments; and the filaments in at least one of said first and said second plurality of filaments have a range of elasticity with a limitation on extension of each of the respective filaments.

2. A membrane according to claim 1 wherein the filaments in said at least one plurality of filaments comprise a core spun thread.

3. A membrane according to claim 1 wherein the filaments in each of said plurality of filaments have a range of elasticity with a limitation on extension of each of the respective filaments.

4. A membrane according to claim 3 wherein the filaments of said first plurality of filaments have a first limitation on extension, and the filaments of said second plurality of filaments have a second limitation on extension, said first limitation on extension being equal to said second limitation on extension.

5. A membrane according to claim 3 wherein the filaments of said first plurality of filaments have a first limitation on extension, and the filaments of said second plurality of filaments have a second limitation on extension, said first limitation on extension differing from said second limitation on extension.

6. A membrane according to claim 3 wherein the filaments in each of said plurality of filaments comprise a core spun thread, the core spun thread having an elastic core thread with a relatively inelastic outer thread spirally wound upon the core thread, the limitation of extension in each of said filaments preventing elongation of the core thread in any one of said filaments beyond an elastic limit of the core thread.

7. A membrane according to claim 6 wherein said layer of breathable material has a maximum permissible limit of distension for prevention of rupture of the layer of breathable material, and the limitations of extension in respective ones of said filaments are less than said maximum permissible limit of distension to prevent the rupture of the layer of breathable material.

8. A membrane according to claim 1 wherein said reinforcing matrix is in contact with said breathable material.

9. A membrane according to claim 1 wherein said cells of said matrix are open cells with uniform cell structure in a condition of the filaments wherein the filaments are in their non-distended state.

10. A textile fabric comprising:

a breathable membrane which is resistive to transport of liquid water and having limited distension in response to a force, the membrane comprising a layer of breathable material resistive to transport of liquid water and a reinforcing matrix of filaments extending in plural directions along said layer of breathable material to inhibit said distension;

a layer of fabric in contact with a surface of said membrane, wherein a first plurality of said filaments intersect a second plurality of said filaments to form cells within said matrix, a minimum cross-sectional dimension of an individual one of said cells being greater by at least approximately an order of magnitude than a diameter of one of said filaments to provide open areas of said layer of breathable material free from obstruction by said filaments; and wherein the filaments in at least one of said first and said second plurality of filaments have a range of elasticity with a limitation on extension of each of the respective filaments.

11. A textile fabric according to claim 10 wherein said reinforcing matrix lies along an interface between said layer of breathable material said layer of fabric.

12. A textile fabric according to claim 10 wherein said nonwoven fabric is in contact with a first surface of said membrane, and said reinforcing matrix lies along a second surface of said membrane opposite said first surface.

13. A garment comprising a breathable membrane which is resistive to transport of liquid water and having limited distension in response to a force, the membrane comprising a layer of breathable material resistive to transport of liquid water and a reinforcing nonwoven matrix of filaments extending in plural directions along said layer of breathable material to inhibit said distension;

wherein a first plurality of said filaments intersect a second plurality of said filaments to form cells within said matrix, a minimum cross-sectional dimension of an individual one of said cells being greater by at least approximately an order of magnitude than a diameter of one of said filaments to provide open areas of said layer of breathable material free from obstruction by said filaments; and wherein the filaments in at least one of said first and said second plurality of filaments have a range of elasticity with a limitation on extension of each of the respective filaments.

14. A garment according to claim 13 further comprising a layer of nonwoven fabric in contact with a surface of said membrane, and wherein said garment is a surgical gown.

15. A garment having a body portion for enclosing the torso of a wearer of the garment, the body portion comprising a breathable membrane which is resistive to transport of liquid water and having limited distension in response to forces, the membrane comprising a layer of breathable material resistive to transport of liquid water and a reinforcing matrix of filaments extending in plural directions along said layer of breathable material to inhibit a distension of said layer of breathable material in any of said plural directions by said forces;

wherein one of said plural directions of extension of a filament is parallel to a spine of the wearer upon a wearing of the garment to inhibit a stretching of said membrane during a bending movement of the wearer;

a first plurality of said filaments intersect a second plurality of said filaments to form cells within said matrix, a minimum cross-sectional dimension of an individual one of said cells being greater by at least approximately an order of magnitude than a diameter of one of said filaments to provide open areas of said layer of breathable material free from obstruction by said filaments; and wherein the filaments in at least one of said first and said second plurality of filaments have a range of elasticity with a limitation on extension of each of the respective filaments.

16. A garment according to claim 15 further comprising a layer of nonwoven fabric in contact with a surface of said membrane.

17. A garment having a limb portion for enclosing a limb of a wearer of the garment, the limb portion comprising a breathable membrane which is resistive to transport of liquid water and having limited distension in response to forces, the membrane comprising a layer of breathable material resistive to transport of liquid water and a reinforcing nonwoven matrix of filaments extending in plural directions along said layer of breathable material to inhibit a distension of said layer of breathable material in any of said plural directions by said forces;

wherein one of said plural directions of extensions of a filament is parallel to a longitudinal axis of said limb upon a wearing of the garment by the wearer to inhibit a stretching of said membrane during a bending movement of said limb;

wherein a first plurality of said filaments intersect a second plurality of said filaments to form cells within said matrix, a minimum diameter of an individual one of said cells being greater by at least approximately an order of magnitude than a diameter of one of said filaments to provide open areas of said layer of breathable material free from obstruction by said filaments; and wherein the filaments in at least one of said first and said second plurality of filaments have a range of elasticity with a limitation on extension of each of the respective filaments.

18. A garment according to claim 17 further comprising a layer of nonwoven fabric in contact with a surface of said membrane.

* * * * *